United States Patent [19]

Banno

[11] Patent Number: 4,587,624
[45] Date of Patent: May 6, 1986

[54] METHOD AND APPARATUS FOR CORRECTING A CURVE RELATING AN ABSORBANCE TO A CONCENTRATION

[75] Inventor: Taiichi Banno, Hachioji, Japan

[73] Assignee: Olympus Optical Co., Ltd., Japan

[21] Appl. No.: 451,419

[22] Filed: Dec. 20, 1982

[30] Foreign Application Priority Data

Dec. 24, 1981 [JP] Japan .................. 56-208047

[51] Int. Cl.[4] ........................... G01N 21/00
[52] U.S. Cl. ...................... 364/571; 364/497; 364/573
[58] Field of Search ............. 356/432, 436, 441, 442, 356/325; 364/497, 498, 571, 573, 526; 204/1 T, 406

[56] References Cited

U.S. PATENT DOCUMENTS

| 3,529,162 | 9/1970 | Troutman | 378/54 X |
| 3,701,601 | 10/1972 | Plumpe, Jr. et al. | 356/436 X |
| 3,724,957 | 4/1973 | Tamate et al. | 356/442 X |
| 3,739,164 | 6/1973 | Bohler | 364/498 X |
| 3,807,875 | 4/1974 | Fischer et al. | 356/432 |
| 3,902,812 | 9/1975 | Honkawa | 356/432 X |
| 4,059,357 | 11/1977 | Klein | 356/432 X |
| 4,064,396 | 12/1977 | Panarello | 364/573 |
| 4,218,746 | 8/1980 | Koshiishi | 204/1 T X |
| 4,238,830 | 12/1980 | Unvala | 364/498 X |
| 4,252,536 | 2/1981 | Kishimoto et al. | 364/497 X |

Primary Examiner—Errol A. Krass
Assistant Examiner—Edward R. Cosimano
Attorney, Agent, or Firm—Parkhurst & Oliff

[57] ABSTRACT

In a colorimetric measurement using a non-linear curve relating an absorbance to a concentration of substance to be measured, the non-linear curve is corrected by measuring an absorbance value $y_6'$ of only one of six standard samples of known different concentrations $x_1$, $x_2 \ldots x_6$ which are used for making the initial non-linear curve, deriving a quotient $\alpha$ by dividing the newly measured absorbance value $y_6'$ by a previously measured absorbance value $y_6$, deriving corrected absorbance values $y_1'$, $y_2' \ldots y_5'$ by producing products $\alpha y_1$, $\alpha y_2 \ldots \alpha y_5$ of the quotient $\alpha$ and previously measured absorbance values $y_1$, $y_2 \ldots y_5$, and by forming a corrected non-linear curve with the aid of the corrected absorbance values $y_1'$, $y_2' \ldots y_5'$ and the newly measured absorbance value $y_6'$.

7 Claims, 4 Drawing Figures

METHOD AND APPARATUS FOR CORRECTING A CURVE RELATING AN ABSORBANCE TO A CONCENTRATION

BACKGROUND OF THE INVENTION

The present invention relates generally to a technique for making a curve relating an absorbance to a concentration of substances to be detected photometrically and more particularly to a method and an apparatus for correcting a non-linear curve which is obtained by using at least three standard samples having known concentration.

As a method of quantitatively analyzing a given substance contained in a sample, there have been developed colorimetric analysis, atomic absorption analysis, fluorometric analysis, luminous spectrum analysis, etc. In these analyses, prior to measurement, a curve relating an absorbance to a concentration of substance is derived by using a plurality of standard samples having known or predetermined concentrations of the relevant substance, and during the actual measurement, a concentration of an unknown sample is derived from a measured absorbance value with reference to the previously derived curve. In usual analysis, the above mentioned curve is obtained by using two standard samples having known different concentrations. That is to say, a linear curve is drawn by connecting two measured absorbance values. However, such a linear curve could not be applied to an analysis which requires a high precision. In this connection, it should be noted that in modern chemical analyzers, the measurement should be effected precisely, because an amount of an available sample is made extremely small. Therefore, in the analysis requiring the high precision, it is preferable to form a non-linear curve relating to an absorbance to a concentration by using at least three standard samples having known different concentrations. That is to say, in a colorimetric analysis for use in a biochemical analysis, four standard samples having known concentrations $x_1$, $x_2$, $x_3$ and $x_4$ are used to derive four absorbance values $y_1$, $y_2$, $y_3$ and $y_4$, respectively and a non-linear curve A representing a mutual relationship between the absorbance and concentration is formed as illustrated in FIG. 1. Hereinafter, this curve is referred to as an absorbance-concentration curve. In case of making the curve by using more than two standard samples, the curve usually becomes a non-linear curve.

In the colorimetric measurement, it has been often encountered that the absorbance value for the same standard sample fluctuates during the measurement due to various causes such as modification of reagent, variation of ambient temperature, secular variation of sample and reagent and fluctuation of light intensity of a light source. Therefore, the absorbance-concentration curve A changes into a curve B shown in FIG. 1. That is to say, even in such a case if the old curve A is used, a concentration of a sample might be erroneously determined to be a smaller value than an actual value. Therefore, the absorbance-concentration curve A must be corrected during the measurement. Heretofore, this correction for the curve is effected by deriving new absorbance values $y_1'$, $y_2'$, $y_3'$ and $y_4'$ for all the four standard samples having the known concentrations $x_1$, $x_2$, $x_3$ and $x_4$ and the new curve B is formed by means of the newly measured absorbance values. However, such a known correcting method has several drawbacks that it is quite cumbersome to measure absorbance values for all standard samples every time the absorbance-concentration curve has to be corrected and thus a treating ability of a whole analyzer becomes lowered, and that error might be introduced in measuring the absorbances of all the standard samples and thus measuring results might be affected.

In case of correcting the linear absorbance-concentration curve, it has been known to shift the curve vertically by an amount equal to a difference between the old absorbance value and the newly measured absorbance value of one standard sample. However, this known correcting technique could not be applied to the non-linear curve, because if so, the non-linear curve might be shifted from an origin at which both the concentration and absorbance values are zero.

SUMMARY OF THE INVENTION

The present invention has for its object to provide a novel and useful method of correcting a non-linear curve relating an absorbance to a concentration of a substance in a simple and precise manner.

It is another object of the invention to provide a method of correcting a non-linear curve relating an absorbance to a concentration with the aid of a smaller number of standard samples than that required for obtaining an initial non-linear curve.

According to the invention, a method of correcting a non-linear curve relating an absorbance to a concentration of substance to be analyzed comprises a step of measuring an absorbance value of at least one standard sample having a known concentration; and a step of correcting the non-linear curve on the basis of said measured absorbance value and an absorbance value which was obtained when the non-linear curve to be corrected was formed.

The present invention also relates to an apparatus for correcting a non-linear curve relating an absorbance to a concentration of a substance to be analyzed and has an object to provide such an apparatus which can correct the curve optimally.

According to the invention, an apparatus for correcting a non-linear curve relating an absorbance to a concentration of a substance to be analyzed comprises means for storing absorbance values of at least three standard samples having known different concentrations;

means for making an initial non-linear curve relating an absorbance to a concentration with the aid of the absorbance values and concentrations of said at least three standard samples;

means for storing an absorbance value of at least one standard sample having a known concentration;

means for calculating at least one correction coefficient with the aid of the stored absorbance values; and means for deriving a corrected non-linear curve relating an absorbance to a concentration with the aid of the calculated correction coefficient and the stored absorbance values.

DESCRIPTION OF THE PREFERRED EMBODIMENTS

Figure 1:
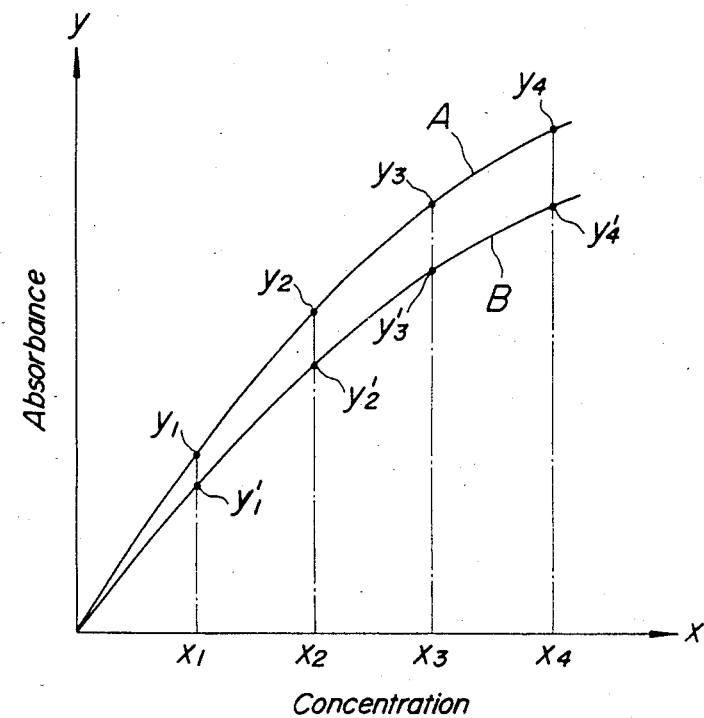
FIG. 1 is a graph for explaining a known method of correcting a non-linear curve relating an absorbance to a concentration of substance to be analyzed.
Figure 2:
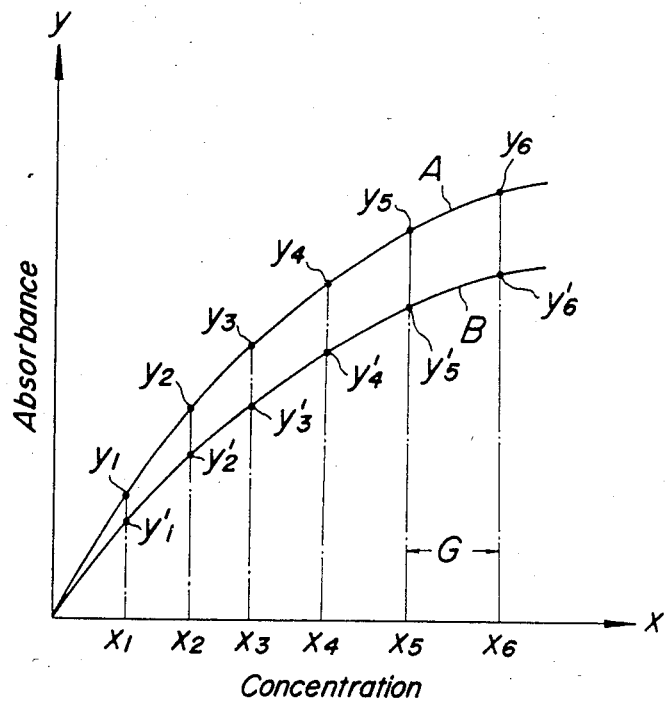
FIG. 2 is a graph showing one embodiment of the non-linear absorbance-concentration curve correcting method according to the invention.

FIG. 2 is a graph showing one embodiment of the correcting method according to the invention. In the present embodiment, an initial non-linear curve A relating an absorbance to a concentration is formed by measuring absorbance values $y_1, y_2, \ldots y_6$ for six standard samples having known different concentrations $x_1, x_2, \ldots x_6$. When the initial curve A is to be corrected during the measurement, one of the six standard samples, for instance, a sixth standard sample having the known concentration $x_6$, is measured to derive a new absorbance value $y_6'$. Then, a quotient $\alpha = y_6'/y_6$ is calculated as a correction coefficient and products $y_5', y_4', y_3', y_2'$ and $y_1'$ of the absorbance values $y_5, y_4, y_3, y_2$ and $y_1$ and $\alpha$, i.e. $y_5' = \alpha \cdot y_5$, $y_4' = \alpha \cdot y_4$, $y_3' = \alpha \cdot y_3$, $y_2' = \alpha \cdot y_2$ and $y_1' = \alpha \cdot y_1$ are calculated. These calculated absorbance values $y_1'$ to $y_5'$ and the newly measured absorbance value $y_6'$ are used as corrected absorbance values and a corrected non-linear curve B is formed with the aid of these corrected absorbance values $y_1'$ to $y_6'$. According to the present embodiment, since the corrected absorbance values $y_1'$ to $y_6'$ are obtained as the products of the measured absorbance values $y_1$ to $y_6$ and the correction coefficient $\alpha$, the corrected curve B passes through the origin at which both the concentration and absorbance are zero. In other words, the correction is not effected in an arithmetic progression manner, but substantially in a geometric progression manner.

According to the invention, the corrected absorbance values $y_1'$ to $y_6'$ are stored and will be used as previously determined absorbance values in a next curve correction.

Figure 3:
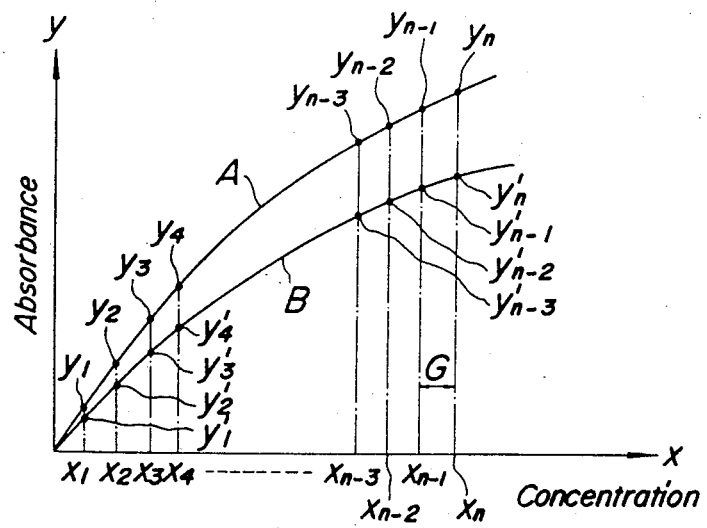
FIG. 3 is a graph illustrating another embodiment of the curve correcting method according to the invention.

FIG. 3 is a graph showing a relation between the absorbance and concentration for explaining another embodiment of the correcting method according to the invention. In the present embodiment, in order to correct an initial non-linear absorbance-concentration curve A which was obtained by measuring absorbance values $y_1, y_2, \ldots y_n$ for n standard samples having known different concentrations $x_1, x_2, \ldots x_n$, respectively (n being larger than three). At first, an absorbance value $y_n'$ for the standard sample having the known maximum concentration $x_n$ is measured. Then a difference $(y_n - y_n')$ between the initial absorbance value $y_n$ and the newly measured absorbance value $y_n'$ is calculated. Next, a quotient $\beta$ of the different $(y_n - y_n')$ and the known concentration $x_n$, i.e. $\beta = (y_n - y_n')/x_n$ is calculated as a correction coefficient. Then, products of the calculated quotient $\beta$ and the known concentrations $x_1, x_2, \ldots x_{n-1}$, i.e.

$$\beta x_1 = (y_n - y_n') \cdot \frac{x_1}{x_n},$$

$$\beta x_2 = (y_n - y_n') \cdot \frac{x_2}{x_n} \ldots \beta x_{n-1} = (y_n - y_n') \cdot \frac{x_{n-1}}{x_n}$$

are calculated. Next, differences between the initial absorbance values $y_1, y_2, \ldots y_{n-1}$ and the products thus obtained are calculated to derive corrected absorbance values $y_1' = y_1 - \beta \cdot x_1$, $y_2' = y_2 - \beta \cdot x_2$, . . . $y_{n-1}' = y_{n-1} - \beta \cdot x_{n-1}$. Finally, a corrected non-linear curve B is formed with the aid of the corrected absorbance values $y_1', y_2', \ldots y_{n-1}'$ and the newly measured absorbance value $y_n'$. In the present embodiment, the differences between the absorbance values $y_1$ and $y_1'$; $y_2$ and $y_2'$; . . . ; $y_{n-1}$ and $y_{n-1}'$; and $y_n$ and $y_n'$ are changed in a geometric progression manner.

In a modified embodiment of the curve correcting method according to the invention explained with reference to FIG. 2, each of intervals G between successive concentration values $x_1, x_2, \ldots x_6$ is divided into sections having widths $g_1, g_2, \ldots g_{p-1}, g_p$ and absorbance values at the sections are derived with the aid of the initial curve A. Then, products of these derived absorbance values and the quotient $\alpha$ are calculated to derive corrected absorbance values. Finally, the corrected curve B is formed with the aid of these corrected absorbance values together with the absorbance values $y_1'$ to $y_6'$. In this modified embodiment, a corrected non-linear curve B may be formed much more accurately, because the number of plotted data points is increased.

Also in a modification of the embodiment of the correcting method according to the invention explained with reference to FIG. 3, each of the intervals G is divided in sections and a number of corrected absorbance values are calculated by using the quotient $\beta$. Then a corrected non-linear curve B is formed with the aid of the thus calculated absorbance values and the corrected absorbance values $y_1', y_2', \ldots y_n'$.

In the above mentioned modifications, the widths of the divided sections $g_1, g_2, \ldots g_{p-1}, g_p$ may be equal to each other, i.e. $g_1 = g_2 = \ldots = g_{p-1} = g_p$, or may be successively decreased or increased, i.e. $g_1 > g_2 > \ldots > g_{p-1} > g_p$ or $g_1 < g_2 < \ldots < g_{p-1} < g_p$.

Further, according to the invention the non-linear curve may be corrected by a combination of the two methods explained with reference to FIGS. 2 and 3. Moreover, in the above embodiments, the correction is effected by using one of the standard samples which were used for obtaining the initial non-linear absorbance-concentration curve A. However, according to the invention, the correction may be equally carried out by using another standard sample which is different from those used for making the initial curve A.

Figure 4:
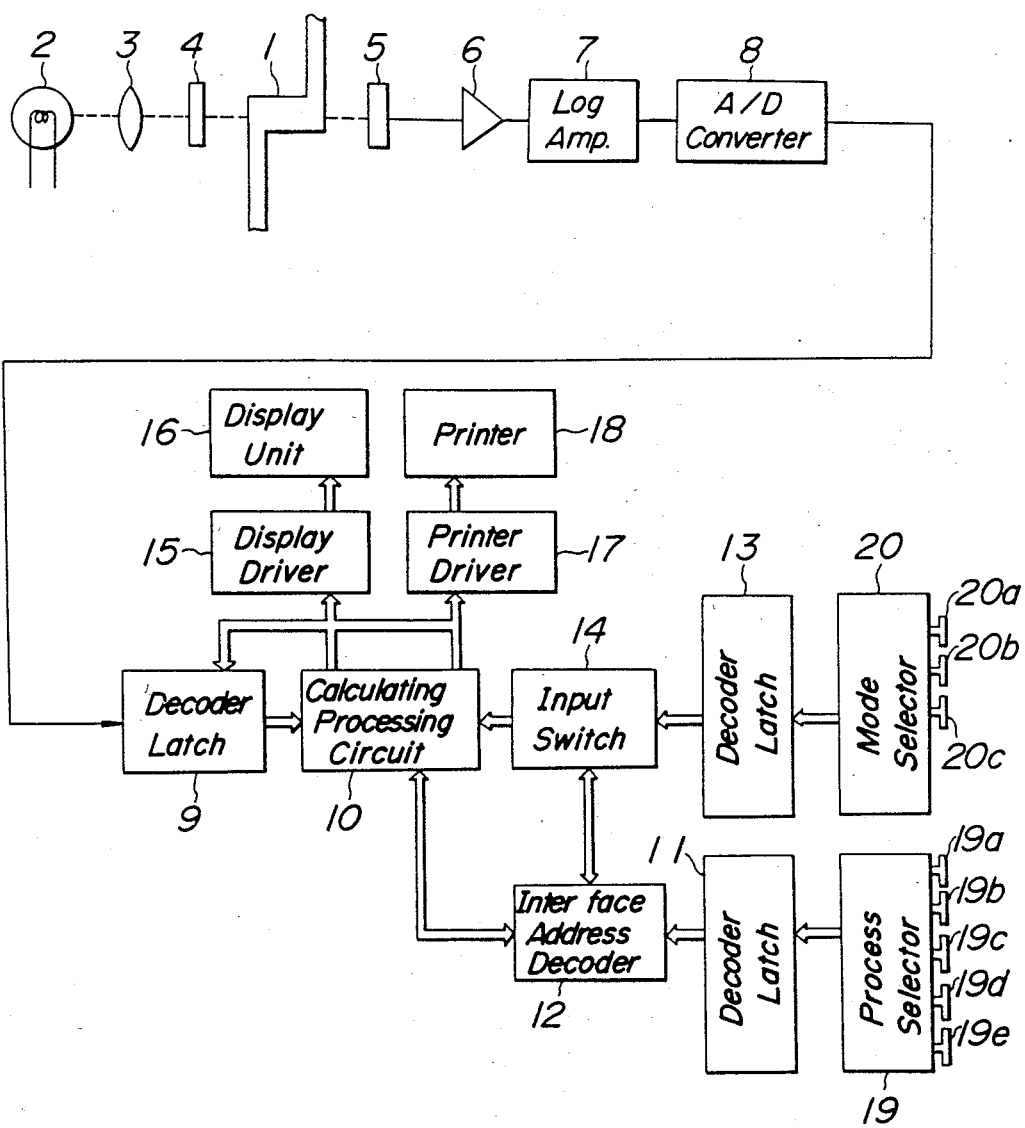
FIG. 4 is a block diagram showing an embodiment of the apparatus for correcting a non-linear absorbance-concentration curve according to the invention.

FIG. 4 is a schematic view illustrating an embodiment of the apparatus for correcting a non-linear absorbance-concentration curve according to the invention provided in a photometric apparatus. In this photometric apparatus, a colorimetric measurement is effected while test liquids and standard sample liquids are conducted into a flow cell 1. A light flux emitted from a light source 2 is projected into the flow cell 1 by means of a lens 3 and an interference filter 4 and a light flux transmitted through the flow cell 1 is made incident upon a photoelectric converting element 5. An output electrical signal from the element 5 is supplied via a pre-amplifier 6 to a logarithmic amplifier 7 to produce an absorbance. The absorbance thus produced is converted by an analog-digital converter 8 into a digital absorbance value which is temporarily stored in a decoder latch circuit 9. The absorbance values are then supplied from the latch circuit 9 to a calculating and processing circuit 10 and are stored and processed therein in accordance with a predetermined program. To the calculating and processing circuit 10 are supplied various kinds of input data from a decoder latch 11 via an interface address decoder 12 and from a decoder latch 13 via an input switch group 14. The decoder latch 11 is coupled with a process selection circuit 19 comprising various operating switches. By suitably operating the switches provided in the process selection circuit 19, it is possible to select one of the predetermined processes for optimally correcting the non-linear curve relating an absorbance to a concentration with the aid of a measured absorbance value of at least one standard sample having a known concentration. By operating the switches in the process selection circuit 19, the following process commands may be inputted to the calculating and processing circuit 10 via the decoder latch 11 and interface address decoder 12.

(1) Command for Process $\alpha$

When a switch 19a is actuated, to the circuit 10 is supplied a command for making a corrected non-linear absorbance-concentration curve B by means of the correction method using the quotient $\alpha$ explained with reference to FIG. 2.

(2) Command for Process $\beta$

When a switch 19b is actuated, there is produced a command for making a corrected curve B with the aid of the correcting method using the quotient $\alpha$ shown in FIG. 3.

(3) Command for First Combined Process of $\alpha$ and $\beta$

When a switch 19c is pushed, there is produced a command for making a corrected curve in accordance with the calculation process $\alpha$ and for checking the corrected curve with the aid of the calculation process $\beta$. The checking may be effected each time the corrected absorbance values are calculated in accordance with the process $\alpha$.

(4) Command for Second Combined Process of $\alpha$ and $\beta$

When a switch 19d is actuated, there is produced a command for making a corrected curve in accordance with the process using the quotient $\beta$ and the corrected curve is checked by means of the process using the quotient $\alpha$.

(5) Command for Sections Intervals

By suitably operating a switch 19e, there is produced a command for dividing the intervals G between successive concentrations into sections having widths $g_1$, $g_2, \ldots g_{p-1}, g_p$ which are $g_1 > g_2 > \ldots > g_{p-1} > g_p$; $g_1 = g_2 = \ldots = g_{p-1} = g_p$; or $g_1 < g_2 < \ldots < g_{p-1} < g_p$.

To the decoder latch 13 is connected a mode selection circuit 20 and by suitably operatig switches provided in this circuit 20 it is possible to supply the following mode commands to the calculating and processing circuit 10 via the decoder latch 13 and input switch group 14.

(1) Command for Manual Mode

By actuating a switch 20a, there is produced a command for manually inputting quotient $\alpha$ and/or $\beta$ for respective concentrations. In this mode of operation, the non-linear curve is automatically corrected by means of the manually inputted quotient $\alpha$ and/or $\beta$. The quotients $\alpha$ and/or $\beta$ can be determined experimentally by taking into account of various factors which might influence upon the curve.

(2) Command for Automatic Mode

When a switch 20b is pushed, there is produced a command for effecting the correction for the curve automatically with the aid of the quotients $\alpha$ and/or $\beta$ which are calculated and stored in the calculating and processing circuit 10.

(3) Command for Coefficient Correction Mode

When a switch 20c is actuated, there is produced a command for correcting the quotients $\alpha$ and/or $\beta$ from an external input. That is to say, in this mode of operation the calculated quotients or manually inputted quotients $\alpha$ and $\beta$ can be corrected into $\alpha \pm \gamma$ and $\beta \pm \epsilon$. The correcting terms $\gamma$ and $\epsilon$ can be experimentally determined in accordance with various factors such as modification of reagent, variation of temperature, kind of reagent to be used, and variation of the light source and photoelectric converting element.

To the calculating and the processing circuit 10 are further connected a display unit 16 via a display driving circuit 15, and a printer 18 via a printer driving circuit 17 so as to display various kinds of information.

According to the curve correcting method of the present invention, the non-linear curve relating an absorbance to a concentration can be simply corrected by deriving an absorbance of at least one standard sample having a known concentration and thus, a working efficiency of an operator can be improved and possible error can be avoided. Therefore, the measurement precision can be increased to a great extent. Moreover, since the various kinds of information can be inputted, the correction can be effected optimally by taking into account of various factors such as the modification of reagent and variation of temperature. Furthermore, since the quotients $\alpha$ and $\beta$ and their correction terms $\gamma$ and $\epsilon$ can be inputted from an external input, it is possible to predict corrected curves and thus, the manner of changing the curves can be previously known for various parameters such as modification of reagent and temperature variation. When the correcting methods of the first and second embodiments are suitably combined with each other, the non-linear curve can be corrected much more precisely.

What is claimed is:

1. A method of determining the concentration of an unknown sample having a non-linear curve relating absorbance to concentration of the unknown sample comprising the steps of:

forming said non-linear curve by using at least three standard samples having known different concentrations;

measuring an absorbance value of only one standard sample of said at least three standard samples having known different concentrations;

correcting the non-linear curve on the basis of said measured absorbance value;

measuring the absorbance value of said unknown sample; and deriving a concentration for said unknown sample from said corrected non-linear curve using the measured absorbance value of said unknown sample.

2. A method according to claim 1, wherein said correcting step comprises:

deriving a difference between the previously determined absorbance value $y_n$ and the newly measured absorbance value $y_n'$ of the same standard sample;

deriving a quotient $\beta$ by dividing said difference $y_n - y_n'$ by the known concentration $x_n$ of the relevant standard sample;

deriving products of the quotient $\beta$ and the known concentrations $x_1, x_2, \ldots x_n$ of the standard samples; and deriving differences between the previously determined absorbance values $y_1, y_2, \ldots y_n$ and said products $\beta x_1, \beta x_2, \ldots \beta x_n$ to produce corrected absorbance values $y_1', y_2', \ldots y_n'$.

3. A method according to claim 2, wherein said newly measured absorbance value $y_n'$ is obtained by measuring the absorbance value of the standard sample having the highest concentration $x_n$.

4. A method according to claim 1, wherein said correcting step comprises:

deriving a quotient $\alpha$ by dividing the newly measured absorbance value $y_n'$ of the standard sample by the previously determined absorbance value $y_n$ of the same standard sample; and deriving products of the quotient $\alpha$ and previously determined absorbance values $y_1, y_2, \ldots y_n$ of the standard samples to produce corrected absorbance values $y_1', y_2', \ldots y_n'$.

5. A method according to claim 4, wherein said newly measured absorbance value is derived by measuring an absorbance value of the standard sample having the highest concentration.

6. A method according to claim 4, wherein said correcting step further comprises:

dividing intervals between successive concentrations into sections having widths $g_1, g_2, \ldots g_p$.

7. A method according to claim 4, wherein said quotient is corrected from an external input.

* * * * *